(12) United States Patent
Yu et al.

(10) Patent No.: US 7,667,060 B2
(45) Date of Patent: Feb. 23, 2010

(54) METHOD OF PRODUCING BIODIESEL

(75) Inventors: Jianqiu Yu, Hong Kong (CN); Deyu Chen, Fuzhou (CN); Junxiong Li, Fuzhou (CN); Zihong Chen, Fuzhou (CN); Gonghao Chen, Fuzhou (CN)

(73) Assignee: Sichuan Gushan Oil Chemical Co. Ltd., Hong Kong (CN)

( * ) Notice: Subject to any disclaimer, the term of this patent is extended or adjusted under 35 U.S.C. 154(b) by 141 days.

(21) Appl. No.: 12/109,451

(22) Filed: Apr. 25, 2008

(65) Prior Publication Data

US 2008/0293956 A1    Nov. 27, 2008

(51) Int. Cl.
*C11C 1/00* (2006.01)
(52) U.S. Cl. .................................. 554/169
(58) Field of Classification Search ............... None See application file for complete search history.

*Primary Examiner*—Deborah D Carr
(74) *Attorney, Agent, or Firm*—Sughrue Mion, PLLC

(57) ABSTRACT

This invention involves a kind of fatty acid methyl ester (bio-diesel fuel), especially the method of obtaining ester-like substances by means of chemical alterations of oil.

2 Claims, 1 Drawing Sheet

METHOD OF PRODUCING BIODIESEL

(I) TECHNICAL FIELD

Figure 1:
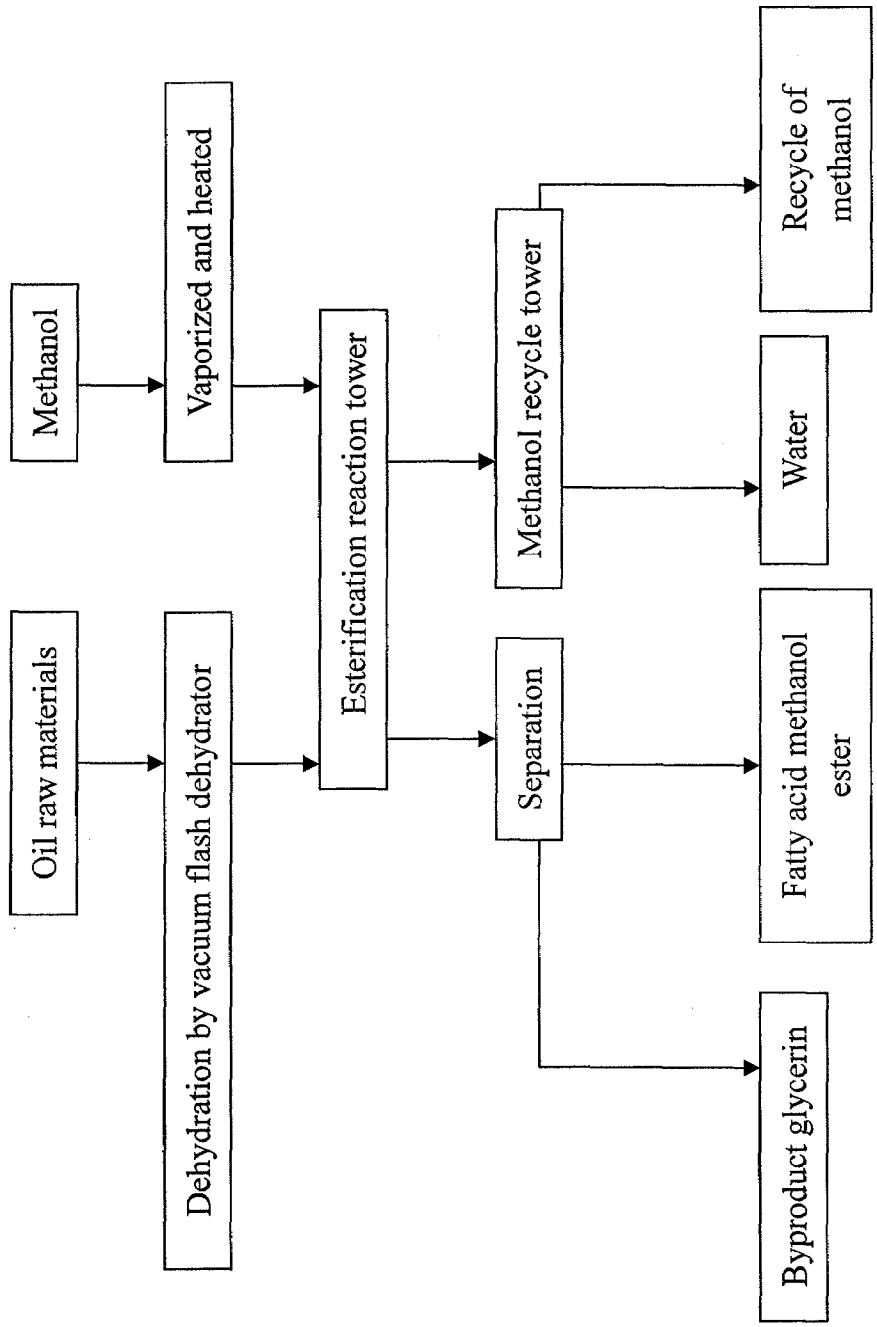

This invention involves a kind of fatty acid methyl ester (bio-diesel fuel), especially the method of obtaining ester-like substances by means of chemical alterations of oil.

(II) BACKGROUND TECHNOLOGIES

Due to the increasing energy consumption and shortage of petroleum resources around the world as well as the soaring oil price, the demand for bio-diesel fuel, a kind of renewable energy source, is increasing day by day. The production is gaining momentum and techniques employed in production mainly involve refinement of the soybean oil, colza oil to the extent that the concentration of free acid achieves less than 0.1%. It is also achieved through synthesizing with methanol solution of alkaline catalyzer by means of ester-exchange reaction.

For raw materials with a high concentration of free fatty acid, the means of alkaline ester exchange reaction isn't applicable. Instead, free fatty acid should be reduced by using acid catalyst ester before the alkaline ester exchange reactions are applied.

Raw materials with high free fatty acid content are also esterified and undergo ester exchange reaction by means of getting mixed with acidic catalysts. Some also adopt the methods of hydrolyzing oil first into fatty acid, then esterifying it with acidic catalysts or by applying pressure. Some others are supercritically esterified under the high temperature and high pressure.

All in all, all the methods have some shortcomings, i.e., the method of alkaline ester exchange reaction is highly costly as it requires refined soybean oil and colza oil as raw materials. Acidic catalyst ester exchange reaction method, which needs enamel facilities due to its strong corrosive property, is not appropriate for production on a large scale and the large amount of sulfuric acid consumption causes severe environmental contamination. High-temperature and high-pressure or supercritical esterification entails advanced alloy materials due to its strong corrosive properties. Hence, a large amount of investment and fairly high energy consumption are required due to immediate cool-down after high-temperature reaction.

(III) BODY

1. Objective: This invention is aimed at providing a kind of method involving synthesizing bio-diesel fuel on a large scale at a low cost for raw materials and processing so as to compensate the short points of the existing technical schemes.
2. Technical scheme: The technical part of this invention is divided into two parts:
① Preliminary treatment of raw materials: After mechanical impurities are removed by filtering, the oil raw materials are stored in the pot of raw materials, where they are transferred by pump before being heated to 160 centigrade by a preheater. Then at −0.09 Mpa they are dehydrated by continuous vacuum flash dehydrator before being esterified.
② Esterification: The dehydrated oil raw materials, with its pressure boosted to 1~4 Mpa by a pump, its temperature added to 110~240 centigrade by a heater, continuously enter into esterification reaction tower from the top. The methanol raw materials are pressured to 1~4 Mpa and heated to 110~240 centigrade after being vaporized, and then continuously enter into esterification reaction tower by way of gas distributor from the bottom of esterification reaction tower. From the top down, oil raw materials meets methanol gas from the bottom up before undergoing a series of chemical reactions and processes such as hydrolyzation, esterification, ester-exchange, gas stripping, absorbing and distillation under the effect of high temperature and high pressure. The water produced from reaction and the residuary methanol is discharged from the top of the tower. The reaction products expelled from the bottom of the Tower are sent to methanol recycle tower by way of the methanol gas produced by reducing pressure and flash vaporizing for recycling methanol. After being esterified, the oil raw materials can be altered at a rate of 98.5%~99.5%. The coarse methyl ester from which glycerin has already been separated undergoes a further process and finally generates bio-diesel fuel of the international standard. Water-containing methanol gas discharged from the top of the tower enters into the methanol recycle tower after being dilated. The recycled methanol will be reused and the generated water from esterification will be discharged from the bottom of the tower.

The theory of this invention goes like this: a series of chemical reactions such as oil hydrolyzation occur from the above to the below in the esterification reaction tower operated continuously with oil raw materials meeting methanol gas in opposite directions, thus fatty acid methanol and glycerin are generated.

Esterification of Fatty Acid:

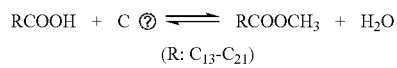

$$\text{RCOOH} + \text{C} \cdot \text{②} \rightleftharpoons \text{RCOOCH}_3 + \text{H}_2\text{O}$$
$$(\text{R: C}_{13}\text{-C}_{21})$$

Exchange of Oil with Methanol Ester:

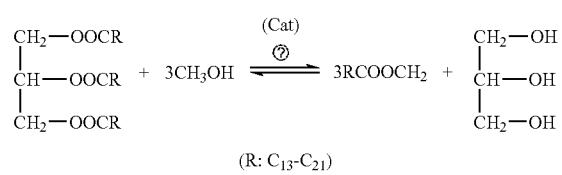

$$(\text{R: C}_{13}\text{-C}_{21})$$

Water generated from fatty acid esterification moves upwards driven by the stripping of methanol gas. Oil hydrolyzation will happen if it meets with oil and the fatty acid generated from hydrolyzation can be esterified when moving downwards and absorbing uprising methanol gas. Nearly all the fatty acid at the middle and down stages of the reaction tower is esterified. Accordingly, here are the places where ester-exchanges of oil and methanol mainly happen and fatty acid methanol and glycerin are generated consequently.

3. Positive Effects: Compared with the method of alkaline ester exchange reaction, this invention can reduce the cost greatly as it can use cheap oil raw material with a high concentration of free fatty acid, while the latter uses refined oil. With acidic catalyst ester exchange reaction method, it provides convenience for continuous production at a large scale as it can use acid-proof steel due to its fairly weak corrosive property to the facilities for not using strong acidic catalyst. However, when compared with the method of ester-exchange reaction under supercritical high temperature and high pressure, it can save investments in facilities due to its weak corrosive property for its fairly low temperature and pressure. It also features low energy consumption, while the latter characterizes high energy-consumption as the reactants of high-temperature reaction require immediate cool-down after the supercritical reaction. It also consumes a small amount of methanol as it adopts the continuous processes of esterification and recycling methanol, thus superfluous methanol can be recycled continuously.

(IV) ATTACHED DIAGRAM

The attached diagram shows the process flow of this invention.

(V) DETAILED PROCEDURES

After being removed of mechanical impurities by filtering, the oil raw materials are then stored in the pot of raw materials, where they are transferred by pump before being heated to 160 centigrade by a preheater. Then at −0.09 Mpa they are dehydrated by continuous vacuum flash dehydrator, then they are pressured to 1~4 Mpa by a pump and heated to 110~240 centigrade, and finally continuously enter into the esterification reaction tower from the top. The methanol raw materials are pressured to 1~4 Mpa with a pump and heated to 110~240 centigrade after being vaporized, and then continuously enter into the esterification reaction tower by way of gas distributor from the bottom of the esterification reaction tower. Oil raw materials from the top oppositely meets methanol gas from the bottom, then undergo a series of chemical reactions and processes such as hydrolyzation, esterification, ester-exchange, gas stripping, absorbing and distillation under the effect of high temperature and high pressure. The water generated from reactions and the residuary methanol is discharged from the top of the tower.

The reaction products expelled from the bottom of the tower are sent to the methanol recycle tower by way of the methanol gas produced by reducing pressure and flash vaporizing for recycling methanol. After being esterified, the oil raw materials can be altered at a rate of 98.5%~99.5%. The coarse methyl ester from which glycerin has already been separated undergoes a further process and finally generates bio-diesel fuel of international standards. Water-containing methanol gas discharged from the top of the tower enters into the methanol recycle tower after being dilated. The recycled methanol will be reused and the generated water from esterification reaction will be discharged from the bottom of the tower.

The detailed processes go like this: Make the concentration of water in oil raw materials fall below 0.1%; the dehydrated oil raw materials, with its pressure boosted to 1~4 Mpa by a pump and its temperature raised to 110~240 centigrade by a heater, continuously enter into the esterification reaction tower from the top. The methanol raw materials (with a concentration of water less than 0.2%) are transferred with its pressure boosted to 1~4 Mpa by a pump and then become methanol gas by means of being vaporized, and then continuously enter into the esterification reaction tower by way of the gas distributor at the bottom of the esterification reaction tower. In the reaction tower, oil raw materials from the top oppositely meets methanol gas from the bottom, then undergo a series of chemical reactions and processes such as oil hydrolyzation, fatty acid esterification, ester-exchange reaction of oil and methanol ester with fatty acid methanol ester and glycerin generated under the middle pressure (1~4 Mpa) and temperature (110~240 centigrade). Superfluous methanol gas, along with water generated from the reaction, is discharged from the top of the reaction tower and recycled by Methanol Recycle Tower continuously for reuse with the generated water from esterification expelled from the bottom of the methanol recycle tower. The reaction product is a mixture of coarse methanol and glycerin discharged from the bottom of the esterification reaction tower. This method can take all kinds of oil with a content of free fatty acid from 0-100% as raw materials, including animal and plant oil at various levels, acid oil-byproduct of refining food oil, wasted oil from restaurants and swill oil. It supports continuous production and intermittent production as well. The reaction tower and methanol recycle tower are incorporated into a system which continuously recycles and purifies the mixture of methanol and water flowing out from the reaction tower for recycling methanol and discharging the water generated from the reaction so as to facilitate the reaction.

The invention claimed is:

1. A method of synthesizing fatty acid methyl ester, comprising the following steps:
   A. subjecting oil raw materials to vacuum dehydration, thereby resulting in dehydrated oil raw materials having a water content of less than 0.1%;
   B. subjecting the dehydrated oil raw materials to a pressure of about 1~4 Mpa thereby resulting in a pressurized dehydrated oil raw material stream, and preheating the pressurized dehydrated oil raw material stream to a temperature of 110~240 centigrade by a heater, continuously feeding the prepared dehydrated oil raw materials into an esterification reaction tower from a top of the esterification reaction tower;
   C. subjecting methanol raw materials having a water content of less than 0.2%, to a pressure of about 1~4 Mpa by a pump thereby resulting in a pressurized methanol raw material, and subjecting the pressurized methanol raw material to vaporization, thereby resulting in a methanol gas stream, and then continuously feeding the methanol gas stream into the esterification reaction tower by way of a gas distributor at a bottom of the esterification reaction tower;
   D. permitting the prepared dehydrated oil raw materials and the methanol gas stream to react in the esterification reaction tower, thereby resulting in synthesis of fatty acid methyl ester and glycerin,
      whereby the prepared dehydrated oil raw materials and the methanol gas stream undergo oil hydrolyzation, fatty acid esterification, and ester exchange reaction in the esterification reaction tower under a pressure of about 1~4 Mpa and a temperature of about 110~240 centigrade;
   E. discharging excessive methanol gas stream along with water generated from the reaction from the top of the esterification reaction tower to a methanol recycle tower; recycling methanol and discharging water generated from esterification from a bottom of the methanol recycle tower; and
   F. discharging a reaction product, wherein the reaction product is a mixture of coarse methyl ester and glycerin, from the bottom of the esterification reaction tower.

2. The method of synthesizing fatty acid methyl ester according to claim 1, wherein the oil raw materials have a content of free fatty acid from 0-100%, and the oil raw materials are selected from the group consisting of animal and plant oil at various levels, acid oil-byproduct of refining food oil, wasted oil from restaurants and swill oil.

* * * * *